United States Patent
Jordan et al.

(10) Patent No.: US 9,301,862 B2
(45) Date of Patent: Apr. 5, 2016

(54) STENT RETRIEVAL MEMBER AND DEVICES AND METHODS FOR RETRIEVING OR REPOSITIONING A STENT

(75) Inventors: Gary A. Jordan, Litchfield, NH (US); Claude O. Clerc, Marlborough, MA (US); Paul K. Norton, Lunenburg, MA (US); Michael Zupkofska, Rockland, MA (US); John J. Damarati, Marlborough, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 569 days.

(21) Appl. No.: 11/341,540

(22) Filed: Jan. 27, 2006

(65) Prior Publication Data
US 2006/0190075 A1    Aug. 24, 2006

Related U.S. Application Data

(60) Provisional application No. 60/647,981, filed on Jan. 28, 2005.

(51) Int. Cl.
*A61F 2/95* (2013.01)
*A61F 2/90* (2013.01)
*A61F 2/88* (2006.01)

(52) U.S. Cl.
CPC ... *A61F 2/95* (2013.01); *A61F 2/90* (2013.01); *A61F 2/885* (2013.01); *A61F 2002/9511* (2013.01); *A61F 2002/9528* (2013.01); *A61F 2002/9534* (2013.01); *A61F 2250/0039* (2013.01)

(58) Field of Classification Search
CPC ............... A61F 2002/9511; A61F 2002/9528; A61F 2002/9534; A61F 2/95
USPC ................................. 623/1.11, 1.15, 1.18, 1.2
See application file for complete search history.

(56) References Cited

U.S. PATENT DOCUMENTS

| | | | | |
|---|---|---|---|---|
| 5,454,834 A | * | 10/1995 | Boebel et al. | 606/228 |
| 5,713,948 A | * | 2/1998 | Uflacker | 623/1.23 |
| 5,755,777 A | * | 5/1998 | Chuter | 623/1.11 |
| 5,919,225 A | * | 7/1999 | Lau et al. | 606/198 |
| 6,013,854 A | * | 1/2000 | Moriuchi | 623/1.11 |
| 6,183,504 B1 | * | 2/2001 | Inoue | 623/1.11 |
| 6,241,757 B1 | * | 6/2001 | An et al. | 623/1.1 |
| 7,252,680 B2 | * | 8/2007 | Freitag | 623/1.12 |

(Continued)

FOREIGN PATENT DOCUMENTS

| | | |
|---|---|---|
| JP | 2003521995 | 7/2003 |
| WO | WO 02/83037 | * 10/2002 |

*Primary Examiner* — Alexander Orkin
(74) *Attorney, Agent, or Firm* — Seager, Tufte & Wickhem LLP

(57) ABSTRACT

An implantable stent includes a stent retrieval member for repositioning or retrieval of the stent after it has been implanted into a bodily lumen. The stent includes a distensible tubular stent having a tubular structure having a tubular wall defined by an interior surface and an exterior surface and having opposed open ends; and a stent retrieval member comprising an elongate member comprising a generally circular perimetric base and a shaped projection having first and second spaced apart members extending acutely or perpendicularly from the base and connected by an apical portion. Force exerted on the shaped projection causes contraction or expansion of the circular base. The circular base is securably attached to one of the open ends of the stent, and the shaped projection extends longitudinally beyond this open end of the stent.

40 Claims, 5 Drawing Sheets

(56) References Cited

U.S. PATENT DOCUMENTS

| 2002/0082683 | A1* | 6/2002 | Stinson et al. | 623/1.23 |
| 2002/0188344 | A1* | 12/2002 | Bolea et al. | 623/1.11 |
| 2003/0040771 | A1* | 2/2003 | Hyodoh et al. | 606/200 |
| 2004/0116996 | A1* | 6/2004 | Freitag | 623/1.11 |
| 2005/0049682 | A1* | 3/2005 | Leanna et al. | 623/1.15 |
| 2006/0100531 | A1* | 5/2006 | Moser | 600/486 |

* cited by examiner

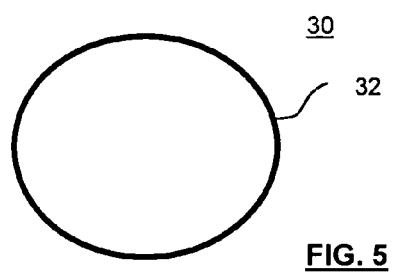
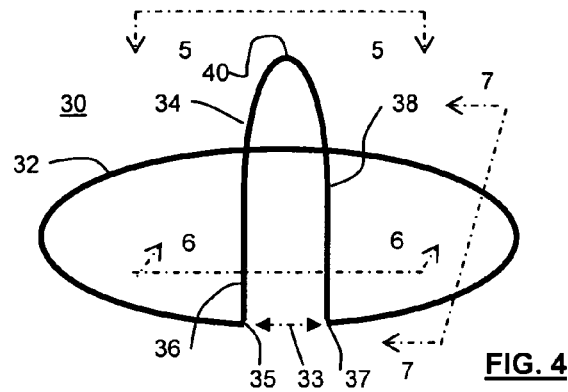
FIG. 5
FIG. 4
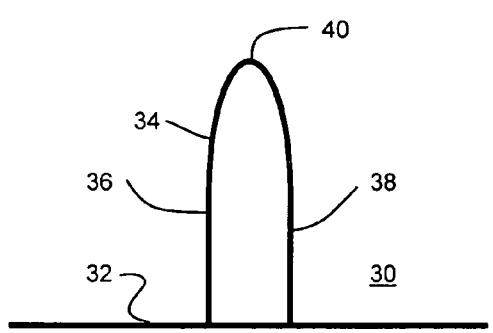
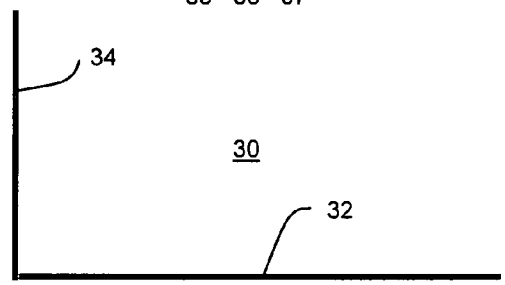
FIG. 6
FIG. 7
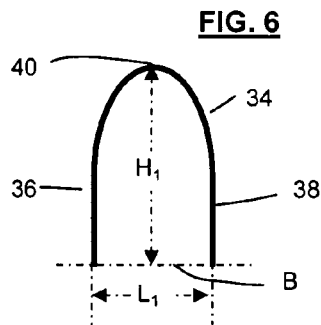
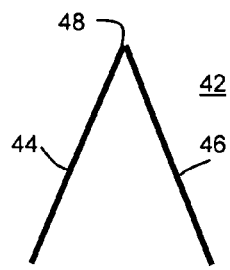
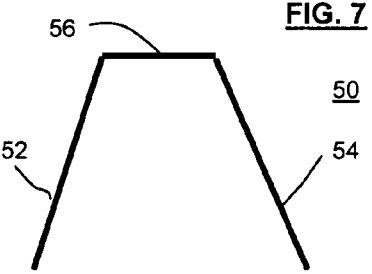
FIG. 8
FIG. 9
FIG. 10
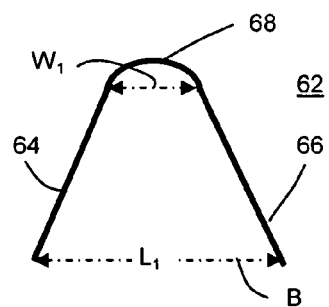
FIG. 11
FIG. 12
FIG. 13

STENT RETRIEVAL MEMBER AND DEVICES AND METHODS FOR RETRIEVING OR REPOSITIONING A STENT

CROSS-REFERENCE TO RELATED APPLICATIONS

This application claims the benefit of U.S. Provisional Application No. 60/647,981, filed Jan. 28, 2005, the contents of which are incorporated herein by reference.

FIELD OF THE INVENTION

The present invention relates to devices, methods and systems for retrieval and/or repositioning of an implanted stent. More particularly, the present invention relates to implantable stents having a stent retrieval member or loop for easy for retrieval and/or repositioning of the implanted stent.

BACKGROUND OF THE INVENTION

An intraluminal prosthesis is a medical device used in the treatment of diseased bodily lumens. One type of intraluminal prosthesis used in the repair and/or treatment of diseases in various body vessels is a stent. A stent is a generally longitudinal tubular device formed of biocompatible material which is useful to open and support various lumens in the body. For example, stents may be used in the vascular system, urogenital tract, esophageal tract, tracheal/bronchial tubes and bile duct, as well as in a variety of other applications in the body. These devices are implanted within the vessel to open and/or reinforce collapsing or partially occluded sections of the lumen.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Structures which have been used as intraluminal vascular grafts have included coiled stainless steel springs; helically wound coil springs manufactured from a heat-sensitive material; and expanding stainless steel stents formed of stainless steel wire in a zig-zag pattern.

Various techniques or systems have been proposed for retrieving and/or repositioning an implanted stent. For example, U.S. Pat. No. 5,643,277 to Soehendra et al. describes the use of a tapered, threaded cable for removal of an implanted stent. The threaded portion of the cable is described as being twisted to engage an implanted biliary stent, such as a polyethylene stent, and then pulled to remove the sent from the patient.

U.S. Pat. No. 6,676,692 to Rabkin et al. describes a catheter system having stent-capturing hooks. The hooks are described as being useful for engaging the stent, thereby allowing repositioning and/or retrieval of the stent.

U.S. Patent Application Publication No. 2002/0188344 A1 to Bolea et al. describes the use of hinged hooks attached to interior portions of an implantable stent. Use of a retrieval tool is described as engaging the hooks, and, upon twisting of the retrieval tool, the stent is contracted thereby allowing retrieval of the stent. In another embodiment, a wire lasso is described as being secured to an implantable stent with the wire lasso having a small loop internally disposed within the open lumen of the stent. The loop of the lasso is described as being engaged by a retrieval tool, and, upon twisting of the retrieval tool, the stent is contracted thereby allowing retrieval of the stent. Other embodiments include a lasso wire threaded through eyelets at a stent end. A retrieval tool is described as engaging the lasso wire, and, upon twisting or axially pulling the lasso wire, the stent is contracted thereby allowing retrieval of the stent.

Prior retrieval systems may appear easy to use, but often require certain user-sensitive techniques, such as twisting or turning in order to reposition or remove the stent. Moreover, in smaller stents, such as biliary stents, the spacing between conventional stent segments is generally smaller than the size of standard forceps or graspers, making it even difficult to grab a hook or lasso.

SUMMARY OF THE INVENTION

The present invention provides a stent retrieval system that allows for easy access to the retrieval member located on an implantable stent. Further, the stent removal member of the present invention avoids complicated twisting movements for retrieval or repositioning of the implanted stent.

In one aspect of the present invention, an implantable distensible band is provided. The band comprises an elongate member comprising a generally circular perimetric base implantable within a bodily lumen and a shaped projection having first and second spaced apart members extending acutely or perpendicularly from the base and connected by an apical portion, whereby force exerted on the shaped projection causes contraction or expansion of the circular base. The elongate member may be a strand, such as a wire strand, either a monofilament or multifilament strand. Desirably, such bands may function as retrieval members when used in conjunction with a stent or a graft.

In another aspect of the present invention, an implantable stent is provided. The stent comprises: (i) a distensible tubular stent having a tubular structure having a tubular wall defined by an interior surface and an exterior surface and having opposed open ends; and (ii) a stent retrieval member comprising an elongate member comprising a generally circular perimetric base and a shaped projection having first and second spaced apart members extending acutely or perpendicularly from the base and connected by an apical portion, whereby force exerted on the shaped projection causes contraction or expansion of the circular base, wherein the circular base is securably attached to one of the open ends of the stent and further wherein the shaped projection extends longitudinally beyond the one open end of the stent.

In another aspect of the present invention, a method of retrieving or repositioning an implanted stent is provided. The method comprises the steps of (a) providing a tubular distensible stent comprising (i) a wall to define an interior surface and an exterior surface and having opposed open ends; and (ii) a stent retrieval member comprising an elongate member comprising a generally circular perimetric base implantable within a bodily lumen and a shaped projection having first and second spaced apart members extending acutely or perpendicularly from the base and connected by an apical portion, whereby force exerted on the shaped projection causes contraction or expansion of the circular base, wherein the circular base is securably attached to one of the open ends of the stent and further wherein the shaped projection extends longitudinally beyond the one open end of the stent; (b) implanting the stent within a bodily lumen; and (c) pulling the shaped projection of the stent retrieval member to contract the first end of the stent and to move the stent.

In another aspect of the present invention, a method of retrieving or repositioning an implanted stent is provided. The method comprises the steps of (a) locating a distensible stent within a bodily lumen, the stent comprising a hollow tubular structure having a tubular wall to define an interior surface and an exterior surface and having opposed open ends and a stent retrieval member comprising an elongate member comprising a generally circular perimetric base implantable within a bodily lumen and a shaped projection having first and second spaced apart members extending acutely or perpendicularly from the base and connected by an apical portion, whereby force exerted on the shaped projection causes contraction or expansion of the circular base, wherein the circular base is securably attached to one of the open ends of the stent and further wherein the shaped projection extends longitudinally beyond the one open end of the stent; and (b) pulling the shaped projection of the stent retrieval member to contract the first end of the stent and to move the stent.

In another aspect of the present invention, a system is provided. The system comprises (a) a distensible stent, said stent comprises (i) a hollow tubular structure having a tubular wall to define an interior surface and an exterior surface and having opposed open ends; and (ii) a stent retrieval member comprising an elongate member comprising a generally circular perimetric base implantable within a bodily lumen and a shaped projection having first and second spaced apart members extending acutely or perpendicularly from said base and connected by an apical portion, whereby force exerted on said shaped projection causes contraction or expansion of said circular base, wherein said circular base is securably attached to one of said open ends of said stent and further wherein said shaped projection extends longitudinally beyond said one open end of said stent; and (b) a delivery catheter for implanting said stent.

BRIEF DESCRIPTION OF THE DRAWINGS

FIG. 4 is a perspective view of a stent retrieval loop according to the present invention having a circular base and a projecting member.

FIG. 5 is a top view of the stent retrieval loop of FIG. 4 taken along the 5-5 axis.

FIG. 6 is a front elevational view of the stent retrieval loop of FIG. 4 taken along the 6-6 axis.

FIG. 7 is a side elevational view of the stent retrieval loop of FIG. 4 taken along the 7-7 axis.

FIG. 8 is an expanded view of the projecting member of FIG. 4.

FIG. 9 is an expanded view of a first alternative design for the projecting member of FIG. 8.

FIG. 10 is an expanded view of a second alternative design for the projecting member of FIG. 8.

FIG. 11 is an expanded view of a third alternative design for the projecting member of FIG. 8.

FIG. 12 is an expanded view of a fourth alternative design for the projecting member of FIG. 8.

FIG. 13 is an expanded view of a fifth alternative design for the projecting member of FIG. 8.

DETAILED DESCRIPTION OF THE PREFERRED EMBODIMENT

Figure 1:
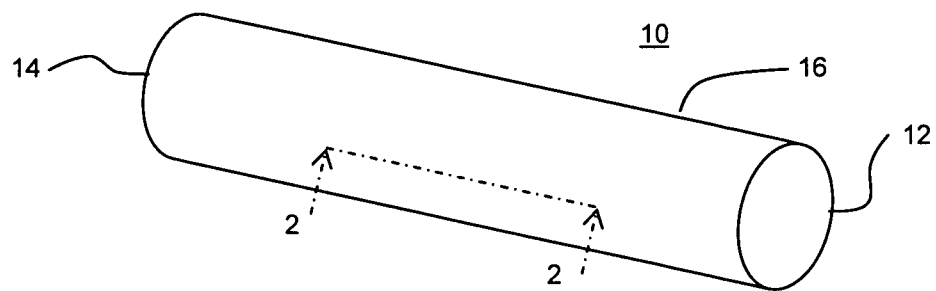
FIG. 1 is a perspective view of a hollow, tubular stent according to the present invention.
Figure 2:
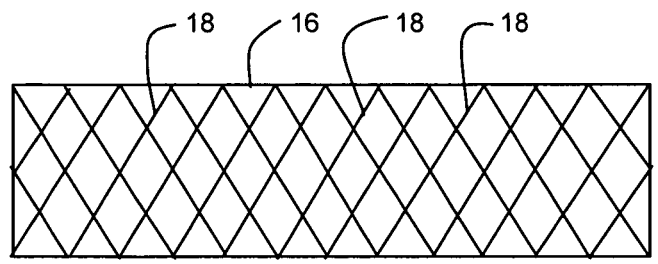
FIG. 2 is an expanded view of a wall portion of the stent of FIG. 1 taken along the 2-2 axis showing a plurality of stent wires.

FIG. 1 depicts stent 10 of the present invention. Stent 10 is a hollow tubular structure having opposed open ends 12, 14 and having a tubular wall 16 therebetween. A portion of the tubular wall 16 is depicted in FIG. 2 as having a plurality of elongate wires 18 formed into the tubular wall 16. The elongate wires 18 traverse the length of the stent 10 in a direction traverse to the longitudinal length of the stent 10. The elongate wires 18 may be formed into the tubular wall 16 by braiding the wires 18, winding the wires 18, knitting the wires 18, and combinations thereof. Preferably, the wires 18 are braided to form the tubular wall 16.

Figure 3:
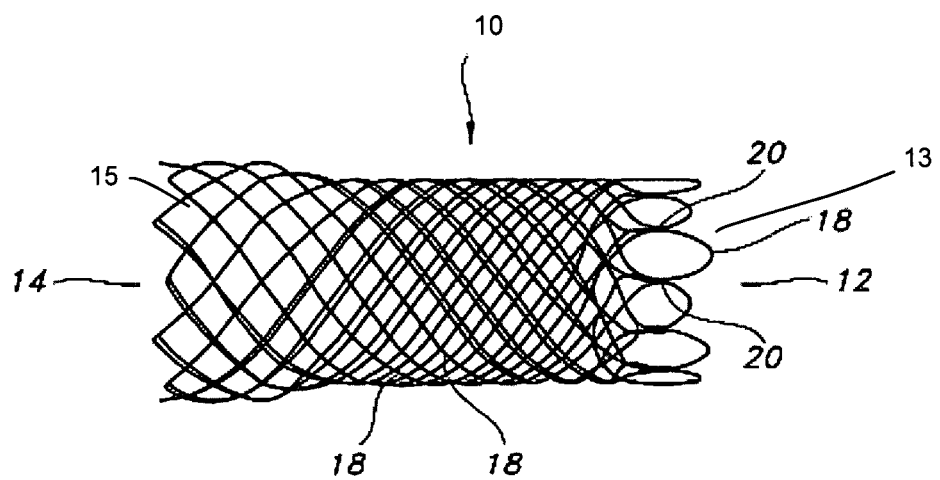
FIG. 3 depicts a braided stent with a closed-end loop design at both stent ends.

As depicted in FIG. 3, stent 10 is desirably an atraumatic stent having no sharp terminating members at one or both of the opposed open ends 12, 14. The elongate wires 18 terminating at open end 12 are mated to form closed loops 13 and adjacently mated wires are secured to one and the other by mechanical means, such as welds 20. The positioning of adjacently mated wires to form closed-loop end designs is further described in U.S. Application No. 60/472,929, filed May 23, 2003, the contents of which are incorporated herein by reference. Desirably, the elongate wires 18 terminating at open end 12 are in a cathedral type arch or loop configuration. Further details of the cathedral type of arch or closed-loop configuration may be found in U.S. application Ser. No. 10/845,844, filed May 15, 2004, the contents of which are incorporated herein by reference.

The stent wires 18 at the open end 14 are bent to form closed loop ends 15 thereat. As depicted in FIG. 3, the loop ends 15 are substantially angular having approximately or about a 90° bend. The radius of curvature at the point of the bend is desirably minimized. In other words, the loop end 15 desirably has an angularly bent portion between substantially straight wire portions that do not otherwise have a portion with a significant radius of curvature. The loop ends 15, however, are not limited to angular bends of 90° and other bend angles may suitably be used. For example, angular bends with a bend angle from about 30° to about 150° are also useful. Other useful bend angles include from about 60° to about 120°, from about 70° to about 10°, from about 80° to about 100°, from about 85° to about 95°, and the like.

The stent 10 depicted in FIG. 3 includes multiple wires, such as 24 wires 18 as depicted in FIG. 3, of nitinol or nitinol-containing material. The wires are relatively thin at a diameter of about 0.011 inches. The number of wires and the diameters of the wires, which may be the same or different, depicted in FIG. 3 are not limiting, and other numbers of wires and other wire diameters may suitably be used.

Desirably, the wires 18 are made from any suitable implantable material, including without limitation nitinol, stainless steel, cobalt-based alloy such as Elgiloy®, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like.

Further, the wires 18 may have a composite construction, such as described found in U.S. Patent Application Publication 2002/0035396 A1, the contents of which is incorporated herein by reference. For example, the wires 18 may have an inner core of tantalum gold, platinum, iridium or combination of thereof and an outer member or layer of nitinol to provide a composite wire for improved radiocapicity or visibility. Preferably, the wires 18 are made from nitinol.

Either of both of the opposed open ends 12, 14 of the stent 10 may have a stent retrieval member 30 securably disposed thereat. A perspective view of a stent retrieval member 30 is depicted in FIG. 4. The stent retrieval member 30, which may also be referred to as a stent retrieval loop, is useful for repositioning and/or retrieval of an implanted or deployed stent 10. The stent retrieval member 30 allows the practitioner to contract and move the stent 10 within the implanted lumen. The stent retrieval member may be made from a memory shape alloy, such as the above described materials, including nitinol. The use of a shape memory material, as compared other convention materials such as suture thread, has numerous advantages. For example, the self-supporting nature of the shape memory material facilitates the locating of the stent retrieval member 30, particularly since it does not sag or flop, but remains substantially stationary once implanted. A memory shape alloy member 30 will not tangle, a potential problem with suture loops, and will also aid in opening the stent 10. Another advantage from using a memory shape alloy material is the wire loop defining the member 30 would be less likely to break than a plastic or polymeric loop when a pulling force is applied, such as required for repositioning or removal of the stent 10.

As depicted in FIG. 4 the stent retrieval member 30 includes a generally circular base 32 and a shaped projection 34. The circular base 32 is a generally circular perimetric base, i.e., in the form of an elongate wire disposed in a generally circular configuration. The circular base 32 may also be described as a generally circular ring. The projection 34 includes first and second spaced apart members 36, 38. The spaced apart members 36, 38 extend from the circular base 32 at a parted region 33 of the circular base 32 and are connected by an apical portion 40 opposed from the circular base 32. The parted region 33 may be described as an interrupted portion of the circular base 32 and is further defined by opposed parted wire ends 35 and 37. The projection 34 extends from the circular base 32 in a substantially perpendicular fashion. The present invention, however, is not limited to a perpendicularly extending projection 32, and as described below other extending orientations may suitably be used.

FIG. 5 depicts a top view of the stent retrieval member 30 of FIG. 4 taken along the 5-5 axis. As depicted in FIG. 5, the stent retrieval member 30 has a circular or a substantially circular base 32. The present invention, however, is not so limited and other shaped bases may suitably be used. Desirably, the shape of the base 32 matches or substantially matches the cross-sectional shape of the stent 10 at either of its opposed open ends 12, 14.

FIG. 6 is a front elevational view of the stent retrieval member 30 of FIG. 4 taken along the 6-6 axis. As depicted in FIG. 6, the shaped projection 32 extends from a substantially planar base 32. FIG. 7 is a right elevational view of the stent retrieval member 30 of FIG. 4 taken along the 7-7 axis. As depicted in FIG. 7, the shaped projection 34 may extend in a substantially perpendicular fashion from the base 32. Further, the shaped projection 34 may also be substantially planar from a side view to reduce the overall profile of the member.

The present invention, however, is not limited to the shaped projection 34 as depicted in FIGS. 4 and 6, and other suitably shaped projections may suitably be used. For example, as depicted in FIG. 8, the length or spacing between the spaced apart members 36, 38 may be increased to form a wider shaped loop with a less pointed or more rounded apical region 40. The shaped projection 34 as depicted in FIG. 8 may also be described as being "U-shaped". Such U-shaped projections may include straight or substantially straight spaced apart members 36, 38 and a curved apical region 40. The present invention, however, is not limited to straight or substantially straight members 36, 38 and other shapes, such as curved or slightly curved, may suitably be used. Such shaped projections 34 may be described as being or lobed-shaped, generally lobed-shaped or substantially lobed-shaped.

Further, as depicted in FIG. 8, the spaced apart members 36, 38 of the shaped projection 34 define an open base, B, of the shaped projection 34. The base B is further defined by a length $L_1$, which is the distance between the members 36, 38 thereat. Further, the apical region 40 defines a height, $H_1$, from base B to the apex or summit of the apical region 40. Desirably, the height, $H_1$, is greater than the length, $L_1$.

As depicted in FIG. 9, a stent retrieval member 42 may include two substantially straight spaced apart members 44, 46. The spaced apart members 44, 46 may be formed from separate members and joined together at the apical region 48 so that the member 48 is in the form of or substantially in the form of a triangle with an open base. Alternatively, the spaced apart members 44, 46 may be formed from a single elongate member and sharply bent at the apical region 48 to form the open triangular shape. Desirably, the members 44 and 46 are of substantially equal lengths. Such a stent retrieval member 42 may also be described as being generally V-shaped. While the apical region 48 is depicted as having a relatively sharp bend, the present invention is not so limited. For example, the apical region 48 may have a curved portion with a radius of curvature.

In another embodiment, a shaped projection 50 may be in the form of a trapezoid. As depicted in FIG. 10, members 52 and 54 of shaped projection 50 as substantially straight segments joined at a planar apical region 56. The lengths of the members 52 and 54 are depicted as being substantially equal in FIG. 10. In such a case, the shaped projection 50 is formed in the shape of an isosceles trapezoid, or a shape substantially representing an isosceles trapezoid, but having an open base opposed from the apical region 56. While the intersection of the members 52 and 54 with the apical region 56 are depicted by sharp bends in FIG. 10, the present invention, however, is not so limited. The bends may be some what rounded, i.e., having some curvature or radius of curvature.

In yet other embodiments as depicted in FIGS. 11 and 12, the shaped projection may be semi-circular, such as shaped projection 58, or semi-elliptical, such as shaped projection 60. Further, as depicted in FIG. 13, shaped projection 62 may include straight members 64 and 66 that are joined by a rounded or curved apical region 68. Further, as depicted in FIG. 13, the spaced apart members 64, 66 of the shaped projection 62 define an open base, B, of the shaped projection 62. The base, B, is further defined by a length $L_1$, which is the distance between the members 64, 66 thereat. Further, the apical region 68 defines a width, $W_1$, which is a distance between the spaced apart members 64, 66 at the apical region 68. Desirably, as depicted in FIG. 13, the length, $L_1$ is greater than the width, $W_1$. Such spaced apart members 64, 68 may also be described as being obliquely disposed to one and the other. The present invention, however, is not so limited, and the width, $W_1$, at the apical region 68 may be greater than the length, $L_1$, between the spaced apart members 64, 66 at the base, B. Further, while the members 64, 66 are depicted in FIG. 13 as being straight or substantially straight, the present invention is not so limited. The members 64, 66 may be curved or slightly curved.

Figure 14:
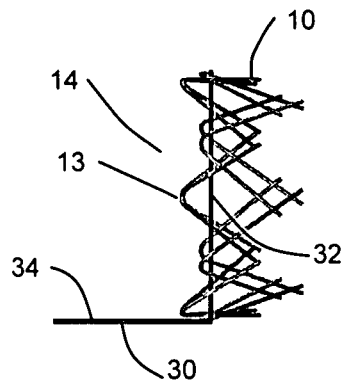
FIG. 14 is a side elevational view of the stent of FIG. 3 having the stent retrieval loop of FIG. 4 at one of the ends of the stent.
Figure 15:
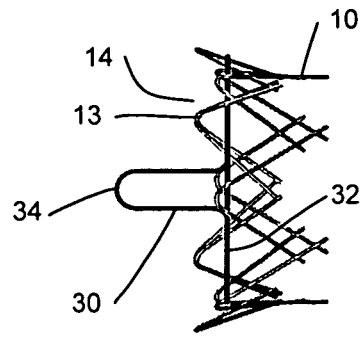
FIG. 15 is a front elevational view of the stent of FIG. 3 having the stent retrieval loop of FIG. 4 at one of the ends of the stent.

As described above, any of the above-described stent retrieval members, such as but not limited to stent retrieval member 30, may be securably disposed or securably attached to either or both of the opposed open ends 12, 14 of the stent 10. As depicted in FIG. 14 stent retrieval member 30 is disposed at the open end 14 of the stent 10. As depicted in FIGS. 14 and 15, the shaped projection 34 extends longitudinally beyond the open end 14 of the stent 10. Such longitudinal projection of the stent retrieval member 30 facilitates grasping of the member 30 by a user for retrieval or repositioning of the stent 10 from a bodily lumen. The closed stent loops 13 at stent end 14 may be equally longitudinally extending or may be longitudinally offset as depicted in FIGS. 14 and 15. The longitudinal offsetting of the stent loops 13 reduces stent deployment force. Such offsetting is described in additional detail in U.S. Provisional Application No. 60/626,729, filed Nov. 10, 2004 and entitled "Atraumatic Stent With Reduced Deployment Force, Method For Making The Same And Method And Apparatus For Deploying And Positioning The Stent", the contents of which is incorporated herein by reference.

Figure 16:
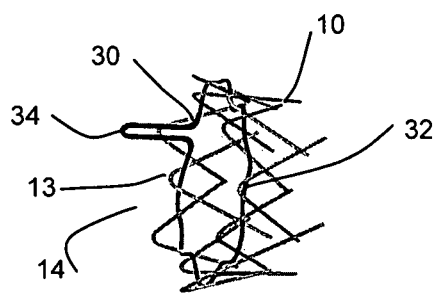
FIG. 16 is a perspective view of the stent of FIG. 3 having the stent retrieval loop of FIG. 4 at one of the ends of the stent.

As depicted in FIG. 16, the stent retrieval member 30 may be securably attached to the stent end 14 by looping the generally circular base 32 through the closed stent loops 13. The elongate wire forming the stent retrieval member 30 may be welded onto itself to form a unitary structure. The present invention, however, is not limited to the use of welding to form a unitary structure, and other joining techniques or methods may suitably be used. For example, portions of the elongate wire forming the stent retrieval member 30 may be joined together through the use of a hypotube (not shown). Alternatively, the elongate wire portions may be crimped or tied in a knot to form a unitary structure.

Figure 17:
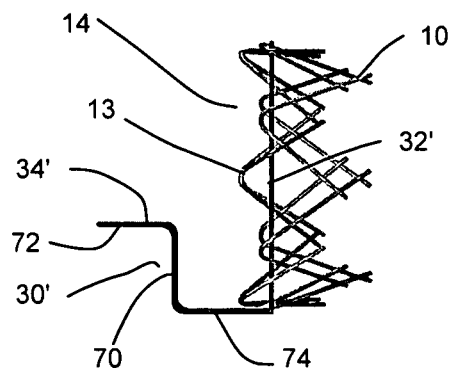
FIG. 17 is a side elevational view of the stent of FIG. 14 having an inwardly projecting stent retrieval loop.
Figure 18:
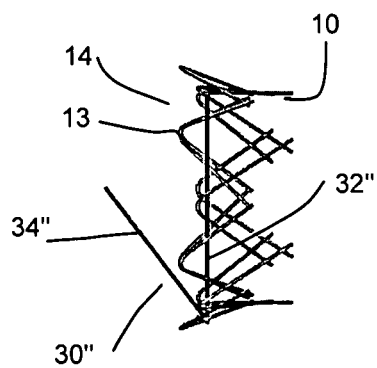
FIG. 18 is a side elevational view of the stent of FIG. 14 having an inwardly and acutely projecting stent retrieval loop.

As described above, the shaped projection 34 may extend perpendicularly or substantially perpendicularly from the generally circular base 32 of the stent retrieval member 30 and generally longitudinally parallel to the wall 16 of the stent 10. The present invention, however, is not so limited. For example, as depicted in FIGS. 17 and 18, shaped projection 34' may be inwardly disposed relative to the interior of the stent 10. For example, the shaped projection 34' of the stent retrieval member 30' may include an inwardly projecting region 70 from which other portions 72 and 74 of the stent retrieval member 34' may be suitably be disposed. The present invention is not limited to the use of the inwardly projecting region 70 for an inwardly projecting stent retrieval member 30'. For example, as depicted in FIG. 18, stent retrieval member 30" may include a shaped projection 34" which is acutely disposed from the base 32" of the stent retrieval member 30".

The memory shape alloy retrieval member or loop 30 may be used with any metal or polymeric stents. The main purpose of the retrieval member or loop 30 is to facilitate movement of the stent once the stent has been deployed. When the projection 34 is pulled along an axis of the stent 10, such as the longitudinal axis of the stent 10, the circular base 32 contracts in diameter to pull the end 14 of the stent 10 radially inward. This action removes the contact force of the end of the stent on the lumen and reduces the profile of the stent for a safe and easy maneuvering of the stent. Once the pulling force on the retrieval loop is removed, the stent self-expands against the lumen in its new position. Desirably, the pulling force excludes any twisting force. Further, the retrieval member 30 desirably does not include any barbs, eyelets or the like so that the member 30 has a low profile and does not interfere with the intended purpose or function of the stent 10.

Figure 16A:
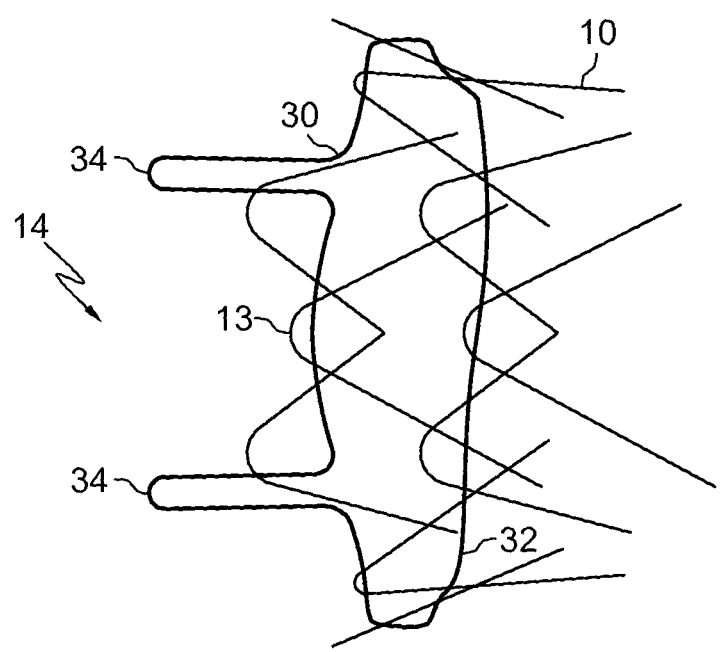
FIG. 16A is a perspective view of the stent of FIG. 3 having the stent retrieval loop of FIG. 4 at one of the ends of the stent and more than one shaped projection.

The stent retrieval member or loop 30 may be made from Nitinol wire wound on a mandrel of the same diameter or larger than the diameter of the end of the stent 10. A larger diameter retrieval loop 30 will have more spring force when placed in or onto a smaller diameter stent. A higher spring force may be desirable because it can facilitate in radially expanding the stent 10, as well as preventing the loop 30 from tangling on the stent. The retrieval member 30 may be shaped with a single protruding projection 34 or with multiple protruding projections 34. A stent retrieval member or loop 30 having more than one protruding projection 34 is depicted in FIG. 16A. As described above, the shape of the protruding projection 34, which may also be referred to as an access loop, may vary in size, angle and wire diameter.

Figure 19:
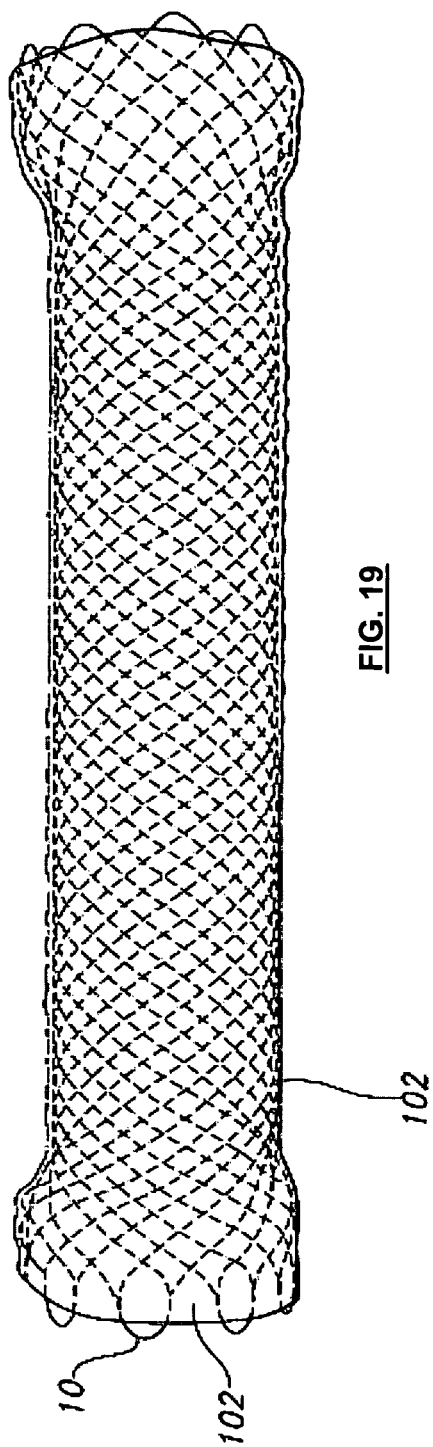
FIG. 19 depicts a stent having a covering of silicone according to the present invention.
Figure 20:
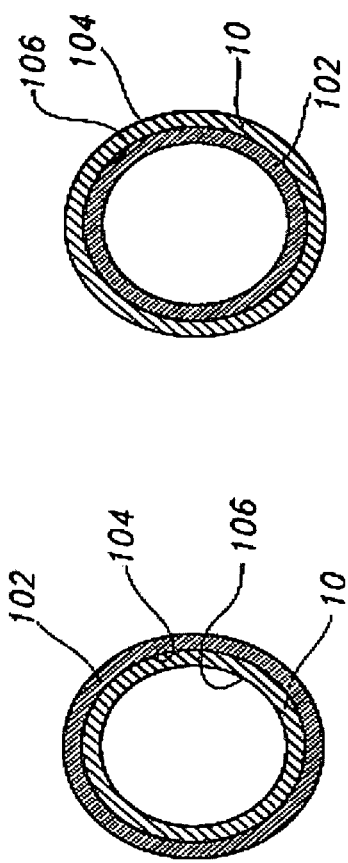
FIG. 20 is a cross-sectional view of the stent of FIG. 19 showing an outer covering of silicone about the stent.
Figure 21:
FIG. 21 is a cross-sectional view of the stent of FIG. 19 showing an inner covering of silicone about the stent.

As depicted in FIG. 19, the stent 10 may be fully, substantially or partially covered or lined with a polymeric material 102. The stent 10 may also be embedded in a polymeric coating. The covering may be in the form of a tubular structure. Nonlimiting examples of useful polymeric materials include polyesters, polypropylenes, polyethylenes, polyurethanes, polynaphthalenes, polytetrafluoroethylenes, expanded polytetrafluoroethylene, silicone, and combinations and copolymers thereof. Desirably, the polymeric material 102 is silicone. The polymeric material and/or silicone 102 may be disposed on external surfaces 104 of the stent 10, as depicted in FIG. 20, or disposed on the internal surfaces 106 of the stent 10, as depicted in FIG. 21, or combinations thereof.

With any embodiment, the stent 10 may be used for a number of purposes including to maintain patency of a body lumen, vessel or conduit, such as in the coronary or peripheral vasculature, esophagus, trachea, bronchi colon, biliary tract, urinary tract, prostate, brain, and the like. The devices of the present invention may also be used to support a weakened body lumen or to provide a fluid-tight conduit for a body lumen.

Also, the stent 10 may be treated with any known or useful bioactive agent or drug including without limitation the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick anti-platelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

Further, with any embodiment of the stent 10 the general tubular shape may be varied. For example, the tubular shape may have a varied diameter, may be tapered, and may have an outwardly flared end and the like. Further, the ends of the stent may have a larger diameter than the middle regions of the stent. In one particularly useful embodiment, at least one of the ends of the stent transition from one diameter to another diameter. Desirably, both ends transition in this manner to yield "flared" ends, as depicted in FIG. 19.

The stent may be coated with a polymeric material. For example, the stent wires may be partially or fully covered with a biologically active material which is elutably disposed with the polymeric material. Further, the polymeric coating may extend over or through the interstitial spaces between the stent wires so as to provide a hollow tubular liner or cover over the interior or the exterior surface of the stent. The polymeric material may be selected from the group consisting of polyester, polypropylene, polyethylene, polyurethane, polynaphthalene, polytetrafluoroethylene, expanded polytetrafluoroethylene, silicone, and combinations thereof.

In one aspect of the present invention, an implantable distensible band is provided. The band comprises an elongate member comprising a generally circular perimetric base implantable within a bodily lumen and a shaped projection having first and second spaced apart members extending acutely or perpendicularly from the base and connected by an apical portion, whereby force exerted on the shaped projection causes contraction or expansion of the circular base. The elongate member may be a strand, such as a wire strand, either a monofilament or multifilament strand. Desirably, such bands may function as retrieval members when used in conjunction with a stent or a graft.

Desirably, the elongate member comprises a biocompatible material selected from the group consisting of nitinol, cobalt-based alloy, stainless steel, platinum, gold, titanium, tantalum, niobium, polymeric materials and combinations thereof. Moreover, the elongate member comprises a biocompatible, shape-memory material, such as a super-elastic material. Desirably, The elongate member comprises nitinol.

The circular base of the implantable distensible band may be parted defining opposed parted ends, wherein the first spaced apart member extends from one of the opposed ends and the second spaced apart member extends from the other the opposed end.

The shaped projection of the implantable distensible band may be U-shaped, V-shaped, shaped as an isosceles trapezoid, shaped as a loop, lobe-shaped, semicircular-shaped, semi-elliptical-shaped, or the like, and combinations thereof.

Desirably, the shaped projection of the implantable distensible band has an open base defined by a length between the spaced apart members and a height of the apical region defined by a length from the open base and the apical region, wherein the height of the apical region is greater that the length of the open base. The shaped projection of the implantable distensible band may also have an open base defined by a length between the spaced apart members and a width of the apical region defined by a lateral length between the spaced apart members at the apical region, wherein the length of the open base is greater than the width of the apical region.

Desirably, the apical region of the implantable distensible band is curved.

Desirably, the spaced apart members of the shaped projection of the implantable distensible band are obliquely disposed to one and the other.

Desirably, the force on the implantable distensible band is a pulling force for contraction of the band, preferably, a pulling force without any twisting force.

In another aspect of the present invention, an implantable stent is provided. The stent comprises: (i) a distensible tubular stent having a tubular structure having a tubular wall defined by an interior surface and an exterior surface and having opposed open ends; and (ii) a stent retrieval member comprising an elongate member comprising a generally circular perimetric base and a shaped projection having first and second spaced apart members extending acutely or perpendicularly from the base and connected by an apical portion, whereby force exerted on the shaped projection causes contraction or expansion of the circular base, wherein the circular base is securably attached to one of the open ends of the stent and further wherein the shaped projection extends longitudinally beyond the one open end of the stent. Desirably, the stent comprises one or more elongate strands braided to form the stent. The plurality of elongate strands may be braided in a series of closed stent loops at the first open end to define an atraumatic stent end, i.e., a stent end having no sharp terminating wires. The circular base of the stent retrieval loop may be securably attached to the closed stent loops at the atraumatic stent end. The circular base may be interlooped with the closed stent loops. Alternatively, or in addition to, portions of the circular base may be welded to the closed stent loops, may be clamped to the closed stent loops, or the like, and combinations thereof.

In this aspect of the present invention, the stent retrieval member may be similarly shaped and made of similar materials as the above-described implantable distensible band. Further, prior to attachment of the stent retrieval member to the stent, the diameter of the circular base of the stent retrieval member may be greater than the diameter of the first open end of the stent. The circular base may contract the open end of the stent upon application of a pulling force upon the shaped projection of the stent retrieval member. Desirably, the force is a pulling force for contraction of the circular base and the first open end of the stent. The force may be a pulling force without any twisting force. The shaped projection of the stent retrieval member may be longitudinally parallel to the wall of the stent or in other words may extend from the stent while being approximately parallel to the stent wall. Alternatively or additionally, the apical region of the shaped projection of the stent retrieval member may be inwardly disposed relative to the interior surface of the stent.

In another aspect of the present invention, a method of retrieving or repositioning an implanted stent is provided. The method comprises the steps of (a) providing a tubular distensible stent comprising (i) a wall to define an interior surface and an exterior surface and having opposed open ends; and (ii) a stent retrieval member comprising an elongate member comprising a generally circular perimetric base implantable within a bodily lumen and a shaped projection having first and second spaced apart members extending acutely or perpendicularly from the base and connected by an apical portion, whereby force exerted on the shaped projection causes contraction or expansion of the circular base, wherein the circular base is securably attached to one of the open ends of the stent and further wherein the shaped projection extends longitudinally beyond the one open end of the stent; (b) implanting the stent within a bodily lumen; and (c) pulling the shaped projection of the stent retrieval member to contract the first end of the stent and to move the stent.

In another aspect of the present invention, a method of retrieving or repositioning an implanted stent is provided. The method comprises the steps of (a) locating a distensible stent within a bodily lumen, the stent comprising a hollow tubular structure having a tubular wall to define an interior surface and an exterior surface and having opposed open ends and a stent retrieval member comprising an elongate member comprising a generally circular perimetric base implantable within a bodily lumen and a shaped projection having first and second spaced apart members extending acutely or perpendicularly from the base and connected by an apical portion, whereby force exerted on the shaped projection causes contraction or expansion of the circular base, wherein the circular base is securably attached to one of the open ends of the stent and further wherein the shaped projection extends longitudinally beyond the one open end of the stent; and (b) pulling the shaped projection of the stent retrieval member to contract the first end of the stent and to move the stent. Desirably, the step of pulling the shaped projection excludes twisting of the shaped projection.

In another aspect of the present invention, a system is provided. The system comprises (a) a distensible stent, said stent comprises (i) a hollow tubular structure having a tubular wall to define an interior surface and an exterior surface and having opposed open ends; and (ii) a stent retrieval member comprising an elongate member comprising a generally circular perimetric base implantable within a bodily lumen and a shaped projection having first and second spaced apart members extending acutely or perpendicularly from said base and connected by an apical portion, whereby force exerted on said shaped projection causes contraction or expansion of said circular base, wherein said circular base is securably attached to one of said open ends of said stent and further wherein said shaped projection extends longitudinally beyond said one open end of said stent; and (b) a delivery catheter for implanting said stent. The system may further comprise forceps for engaging the shaped projection of the stent retrieval member.

Various stent types and stent constructions may be employed in the invention. Among the various stents useful include, without limitation, self-expanding stents and balloon expandable extents. The stents may be capable of radially contracting, as well and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents. The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like. Examples of various stent configurations are shown in U.S. Pat. No. 4,503,569 to Dotter; U.S. Pat. No. 4,733,665 to Palmaz; U.S. Pat. No. 4,856,561 to Hillstead; U.S. Pat. No. 4,580,568 to Gianturco; U.S. Pat. No. 4,732,152 to Wallsten, U.S. Pat. No. 4,886,062 to Wiktor, and U.S. Pat. No. 5,876,448 to Thompson, all of whose contents are incorporated herein by reference.

The invention being thus described, it will now be evident to those skilled in the art that the same may be varied in many ways. Such variations are not to be regarded as a departure from the spirit and scope of the invention and all such modifications are intended to be included within the scope of the following claims.

What is claimed is:

1. An implantable stent comprising:
   a distensible tubular stent having a tubular structure having a tubular wall defined by an interior surface and an exterior surface and having opposed first and second open ends; and
   a stent retrieval member comprising a self-supporting elongate member comprising a generally circular perimetric base and two shaped projections, each shaped projection having first and second spaced apart members extending perpendicularly from said base and connected by an apical portion, whereby force exerted on said shaped projections causes contraction or expansion of said circular base,
   wherein said circular base is securably attached to said tubular wall of said stent,
   wherein each of said shaped projections extends longitudinally away from said tubular wall and past one of said first or second open ends of said stent,
   wherein said shaped projection of said stent retrieval member is approximately parallel to the stent wall.

2. The stent of claim 1, further comprising one or more elongate strands braided to form said stent.

3. The stent of claim 2, wherein said plurality of elongate strands are braided in a series of closed stent loops having angular bends at said first open end to define an atraumatic stent end.

4. The stent of claim 3, wherein said circular base of said stent retrieval member is securably attached to said closed stent loops at said atraumatic stent end.

5. The stent of claim 4, wherein said circular base is interlooped with said closed stent loops.

6. The stent of claim 4, wherein portions of said circular base are welded to said closed stent loops.

7. The stent of claim 4, wherein portions of said circular base are clamped to said closed stent loops.

8. The stent of claim 1, wherein said elongate member of said stent retrieval member is a strand.

9. The stent of claim 1, wherein said elongate member of said stent retrieval member comprises a biocompatible material selected from the group consisting of nitinol, cobalt-based alloy, stainless steel, platinum, gold, titanium, tantalum, niobium, polymeric materials and combinations thereof.

10. The stent of claim 1, wherein said elongate member of said stent retrieval member comprises a super-elastic material.

11. The stent of claim 1, wherein said elongate member of said stent retrieval member comprises nitinol.

12. The stent of claim 1, wherein said circular base is parted defining opposed parted ends and further wherein a first spaced apart member of a first of the two shaped projections extends from one of said opposed ends and a second spaced apart member of the first of the two shaped projections extends from the other said opposed end.

13. The stent of claim 12, wherein said shaped projection of said stent retrieval member is U-shaped.

14. The stent of claim 12, wherein said shaped projection of said stent retrieval member is V-shaped.

15. The stent of claim 12, wherein said shaped projection of said stent retrieval member is shaped as an isosceles trapezoid.

16. The stent of claim 12, wherein said shaped projection of said stent retrieval member is shaped as a loop.

17. The stent of claim 12, wherein said shaped projection of said stent retrieval member is lobe-shaped.

18. The stent of claim 12, wherein said shaped projection of said stent retrieval member is semicircular-shaped.

19. The stent of claim 12, wherein said shaped projection of said stent retrieval member is semi-elliptical-shaped.

20. The stent of claim 12, wherein each of the two shaped projections of said stent retrieval member has an open base defined by a length between said spaced apart members and a height of said apical region defined by a length from said open base to said apical region, wherein said height of said apical region is greater that said length of said open base.

21. The stent of claim 12, wherein each of the two shaped projections of said stent retrieval member has an open base defined by a length between said spaced apart members and a width of said apical region defined by a lateral length between said spaced apart members at said apical region, wherein said length of said open base is greater than said width of said apical region.

22. The stent of claim 12, wherein, prior to attachment of said stent retrieval member to said stent, the diameter of said circular base of said stent retrieval member is greater than the diameter of said first open end of said stent.

23. The stent of claim 12, wherein said circular base contracts said first open end of said stent upon application of a pulling force upon said shaped projection of said stent retrieval member.

24. The stent of claim 1, wherein said apical region of each of the two shaped projections is curved.

25. The stent of claim 1, wherein said spaced apart members of each of the two shaped projections are obliquely disposed to one and the other.

26. The stent of claim 1, wherein said apical region of said shaped projection of said stent retrieval member has is inwardly disposed relative to said interior surface of said stent.

27. The stent of claim 1, wherein said force is a substantially non-twisting pulling force for contraction of said circular base and said first open end of said stent.

28. The stent of claim 1, wherein said circular base is securably attached to said tubular wall at one side of said first open end of said stent.

29. A system comprising:
(a) a distensible stent, said stent comprising:
(i) a hollow tubular structure having a tubular wall to define an interior surface and an exterior surface and having opposed first and second open ends; and
(ii) a stent retrieval member comprising a self-supporting elongate member comprising a generally circular perimetric base implantable within a bodily lumen and two shaped projections, each shaped projection having first and second spaced apart members extending perpendicularly from said base and connected by an apical portion, whereby force exerted on said shaped projection causes contraction or expansion of said circular base,
wherein said circular base is securably attached to said tubular wall of said stent,
wherein each of said shaped projections extends longitudinally away from said tubular wall and past one of said first one or second open ends of said stent, and
wherein said shaped projection of said stent retrieval member is approximately parallel to the stent wall; and
(b) a delivery catheter for implanting said stent.

30. The system of claim 29 further comprising:
forceps for engaging said shaped projection of said stent retrieval member.

31. The system of claim 29, wherein said circular base is securably attached to said tubular wall at one side of said first open end of said stent.

32. An implantable stent comprising:
a distensible tubular stent comprising one or more elongate strands braided or wound to define a tubular structure having a tubular wall defined by an interior surface and an exterior surface and having opposed first and second open ends; and
a stent retrieval member comprising an elongate member comprising a generally circular perimetric base and two shaped projections, each shaped projection having first and second spaced apart members extending perpendicularly from said base and connected by an apical portion, whereby force exerted on said shaped projections causes contraction or expansion of said circular base,
wherein said one or more elongate strands are angular bent with a bend angle from about 30° to about 150° in a series of closed stent loops at said first open end to define an atraumatic stent end,
wherein said circular base is securably attached to said tubular wall at one or more of the closed stent loops at said first open end of said stent,
wherein said shaped projections extend longitudinally away from said tubular wall and past an opposed side of said first one open end of said stent, and
wherein said shaped projections of said stent retrieval member are approximately parallel to the stent wall.

33. The stent of claim 32, wherein said circular base is interlooped with said one or more closed stent loops.

34. The stent of claim 32, wherein said circular base is parted defining opposed parted ends and further wherein said first spaced apart member extends from one of said opposed ends and said second spaced apart member extends from the other said opposed end.

35. The stent of claim 34, wherein said shaped projections of said stent retrieval member are selected from the group consisting of a V-shaped projection, a V-shaped projection, an isosceles-trapezoid-shaped projection, a loop-shaped projection, a lobe-shaped projection, a semicircular-shaped projection or a semi-elliptical-shaped projection.

36. The stent of claim 32, wherein said elongate member of said stent retrieval member comprises a super-elastic material.

37. The stent of claim 32, wherein said elongate member of said stent retrieval member comprises nitinol.

38. The stent of claim 32, wherein said elongate member of said stent retrieval member is a metallic strand selected from the group consisting of a monofilament metallic strand or a multifilament metallic strand.

39. The stent of claim 32, wherein said elongate member of said stent retrieval member does not include any barbs or eyelets.

40. The stent of claim 32, wherein said force is a substantially non-twisting pulling force for contraction of said circular base and said first open end of said stent.

* * * * *